US000001039H

United States Statutory Invention Registration [19]

[11] Reg. Number: H1039

[43] Published: Apr. 7, 1992

Tripp, Jr. et al.

[54] INTRUSION-FREE PHYSIOLOGICAL CONDITION MONITORING

[75] Inventors: Lloyd D. Tripp, Jr., Dayton; William B. Albery, Kettering, both of Ohio; Richard E. Ellison, Maryland Heights, Mo.

[73] Assignee: The United States of America as represented by the Secretary of the Air Force, Washington, D.C.

[21] Appl. No.: 172,146

[22] Filed: Nov. 14, 1988

[51] Int. Cl.[5] ..... A62B 18/02

[52] U.S. Cl. ..... 128/206.28; 128/202.16; 128/201.23; 128/633

[58] Field of Search ..... 128/633, 634, 637, 201.23, 128/201.24, 201.29, 202.11, 204.23, 204.29, 206.21, 206.28; 340/495; 244/196, 197

[56] References Cited

U.S. PATENT DOCUMENTS

| | | | |
|---|---|---|---|
| 2,414,747 | 1/1947 | Kirshbaum | 128/633 |
| 2,706,927 | 4/1955 | Wood | 88/14 |
| 3,638,640 | 2/1972 | Shaw | 128/633 |
| 3,998,550 | 12/1976 | Konishi et al. | 356/39 |
| 4,407,290 | 10/1983 | Wilber | 128/633 |
| 4,603,700 | 8/1986 | Nichols et al. | 128/633 |
| 4,621,643 | 11/1986 | New, Jr. et al. | 128/633 |
| 4,651,728 | 3/1987 | Gupta et al. | 128/204.29 |
| 4,714,341 | 12/1987 | Hamaguri et al. | 356/41 |
| 4,770,179 | 9/1988 | New, Jr. et al. | 128/633 |

OTHER PUBLICATIONS

"Comparison of Time-Resolved and-Unresolved Measurements of Deoxyhemoglobin in the Brain" by Chance et al.; Biochemistry, vol. 85, Jul. 1988, pp. 4971–4975.

*Primary Examiner*—Michael J. Carone

*Attorney, Agent, or Firm*—Donald J. Singer; Bernard E. Franz; Gerald B. Hollins

[57] ABSTRACT

A physiological well-being monitoring system especially suited for use by the pilot or other aircrew members of a high-performance aircraft such as a tactical aircraft is disclosed. The monitoring arrangement includes non-invasive sensing of arterial blood supply in the cranial adjacent portions of the pilot's body through the use of pulsating vascular bed optical signal transmission. The signal transmission is accomplished by way of sensors included in a pilot invisible and non-obstructing modification of, for example, the oxygen mask portion of the pilot life-support apparatus. Use of the physiological monitoring signals to generate alarm or assume control of the aircraft is also disclosed along with representative data associated with the sensed pilot physiological well-being indicators.

15 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

INTRUSION-FREE PHYSIOLOGICAL CONDITION MONITORING

RIGHTS OF THE GOVERNMENT

The invention described herein may be manufactured and used by or for the Government of the United States for all governmental purposes without the payment of any royalty.

BACKGROUND OF THE INVENTION

This invention relates to the field of non-intrusive, non-invasive physiological monitoring of a human test subject and particularly to the monitoring of cranial region physiological conditions in the aircrew members of high performance aircraft.

G-force induced loss of consciousness (GLOC), an extreme example of physiological deterioration, has been found to be second only to the phenomenon of spatial disorientation in the priority of human factors threats facing aircrew members of a modern tactical aircraft. GLOC, in fact, is believed to be one of the primary causes of present-day tactical aircrew fatalities notwithstanding the use of anti-G suits and a number of other human factor improvements in the modern fighter aircraft. Each increment of aircraft performance improvement since the early 1900's has, in fact, been accompanied by an increased measure of danger from this source to aircrew members with the threshold of GLOC having been crossed at least in the early 1920's or some 65 years ago. The U.S. military, particularly the U.S. Air Force and U.S. Navy, have been active in advancing the loss of consciousness prevention art as is exemplified, for example, by numerous issued patents relating to anti-G-force suits and other G-force threat minimizing apparatus. The major concern with which GLOC and other human stress problems are regarded in modern tactical aircraft is also exemplified by the reclined seat, advanced anti-G suit servo valves, G limiting flight control computer, and other human factors considerations that are standard equipment in the F-16 and other present-day tactical aircraft.

Notwithstanding these efforts, however, there has heretofore been a notable absence of satisfactory operational loss of consciousness monitoring arrangements for aircrew members. Principally, this absence arises because such monitoring has been considered to necessarily involve the use of either anatomically invasive instrumentation devices or at best, the use of dermal sensing electrodes. Such arrangements are, of course, highly disfavored or even considered to be physiologically and psychologically threatening by aircrew members.

To be acceptable in an aircraft operational environment, it is necessary that the physiological condition monitoring arrangement be totally invisible or unobtrusive to an aircrew member. In addition to this non-interfering nature of practical GLOC monitoring equipment, the meaningful use of such equipment is, for example, to actuate an alarm system or activate an automatic pilot system and assume control of the aircraft. This demands that an employed GLOC system be both highly reliable and impeccably accurate. Accuracy of this degree, for example, goes well beyond the bounds of sensing the G-force loading incurred by the aircraft and its crew members. Such accuracy requires that real time individual responses of crew members, notwithstanding person to person variations and variations in the physiological resilience of a given person from time to time be considered.

One of the more promising approaches to such improvement in the GLOC and physiological monitoring of an aircrew member involves extension of the oximeter instrumentation commonly used in patient monitoring systems in a modern hospital into the arena of aircrew physiological monitoring. A first-blush consideration of this extension, however, incurs difficulty with a need for intimately placed and often, subjectively located anatomical sensors in the case of monitored hospital patients. This necessity of intimate sensors for the hospital oximeter has, in fact, prompted the principal usage of such instrumentation to be with unconscious or severely movement restrained patients in the hospital setting. In one frequently used oximeter system, for example, the presence of patient movement and the resulting spurious signals received at the oximeter has prompted the use of EKG related signals, (signals derived from chest electrodes) as a timing trigger source to increase oximeter reliability. Clearly, arrangements of this type are unsuitable for use in an operational aircraft environment.

The usefulness of the oximeter instrument in a hospital setting is illustrated by a number of U.S. patents which relate to the oximeter instrument. Included in these patents are several relating to the probe or transducer device used in collecting oximeter or physiological condition signals from a person—e.g. the following patents: U.S. Pat. Nos. 4,770,179; 4,700,708; 4,685,464; 4,621,643; 4,167,331; 3,998,550; 3,847,483; 3,704,706; 3,638,640.

In addition to these probe related patents, many of which are concerned with the need for a low-cost disposable and sterile probe in the hospital environment, the patent art includes a number of documents relating to various aspects of the oximeter monitoring system in general. Several of these patents describe the operating theory and other aspects of designing a practical oximeter instrument. Included in these overall system documents are the following U.S. patents:

- U.S. Pat. No. 4,714,341—"Multi-Wavelength Oximeter Having a Means for Disregarding a Poor Signal" issued to K. Hamaguri et al.
- U.S. Pat. No. 4,653,498—"Pulse Oximeter Monitor" issued to W. New, Jr. et al.
- U.S. Pat. No. 4,603,700—"Probe Monitoring System for Oximeter" issued to R. A. Nichols et al.
- U.S. Pat. No. 4,266,554—"Digital Oximeter" issued to K. S. Hamaguri et al.
- U.S. Pat. No. 4,407,290—"Blood Constituent Measuring Device and Method" issued to S. A. Wilber.
- U.S. Pat. No. 3,704,706—"Heart Rate and Respiratory Monitor" issued to P. R. Herczfeld et al.
- U.S. Pat. No. 3,998,550—"Photoelectric Oximeter" issued to M. Koniski et al.
- U.S. Pat. No. 2,706,927—"Apparatus for Determining Percentage Oxygen—Saturation of Blood" issued to E. H. Wood et al.

The disclosure of this group of overall oximeter system patents is hereby incorporated by reference into the present specification.

Notwithstanding these examples of inventive attention to oximeter related instruments, the patent art has failed to provide a satisfactory operational physiological monitoring system for the pilot or other aircrew member of a high-performance aircraft.

SUMMARY OF THE INVENTION

In the present invention, the pilot of a tactical aircraft is provided with a non-invasive and invisible cerebral region physiological state monitoring arrangement that involves new optical sensing elements disposed in existing pilot life-support apparatus and coupled to electronic processing circuitry of the type employed in state-of-the-art hospital patient oximetry processors.

It is an object of the present invention, therefore, to provide a non-invasive, invisible physiological monitor for a pilot or aircrew member of a high-performance aircraft.

It is another object of the invention to provide a cranial region physiological monitoring arrangement which employs non-invasive optical sensing of cranial region elements of a monitored person.

It is another object of the invention to provide cranial region physiological monitoring which employs sensing elements that are disposed in existing pilot life-support apparatus.

It is another object of the invention to provide cranial region physiological monitoring sensors which employ solid-state energy transducers that are disposed in the oxygen mask of the monitored aircrew member.

It is another object of the invention to provide a cranial region physiological monitoring arrangement which is based on sensing the coloration and density variations of a pulsating vascular bed region that is disposed in the nose structure of a person.

It is another object of the invention to provide a cranial region physiological monitoring arrangement for a pilot which operates by sensing coloration differences between oxygenated and deoxygenated hemoglobin.

It is another object of the invention to provide a physiological monitoring apparatus that is responsive to the quantitative presence of hemoglobin in an internal carotid artery connected pulsating vascular bed region of a monitored aircrew member.

It is another object of the invention to provide a physiological monitoring apparatus which operates in response to circulatory conditions in the nasal septal anterior ethmoid artery of a monitored aircrew member.

It is another object of the invention to provide a physiological state monitoring arrangement in which physiological sensing signal conductors can be combined with existing communication conductors in a common tether cable that is of minimal encumbrance to an aircraft pilot It is another object of the invention to provide a pilot physiological monitoring arrangement that employs a two spectral frequency optical monitoring of a pulsating vascular bed region in the pilot.

It is another object of the invention to provide a physiological monitoring system which may be used for detecting loss of consciousness, mental impairment and other physiological disability conditions in an aircraft pilot.

It is another object of the invention to provide a physiological monitoring arrangement which generates a signal that may be combined with additional physiological signals to generate a verified physiological danger signal.

Additional objects and features of the invention will be understood from the following description and the accompanying drawings.

These and other objects of the invention are achieved by aviation life-support apparatus comprising the combination of a facial mask member receivable over the nose and lower facial region including the mouth and nose apertures of a human test subject; means for communicating a flow of oxygen inclusive breathing gases to and from said mask member and said human test subject; acoustic to electrical transducer means received in said mask member in acoustic communication with said human test subject for generating electrical signals representative of test subject generated vocal sounds; optical sensing means received in said mask member and in optical communication with a facial region pulsating vascular bed of said test subject for sensing G-force influenced quantitative blood flow indicators in said vascular bed and the adjacent cerebral regions of said test subject.

DETAILED DESCRIPTION

Figure 1:
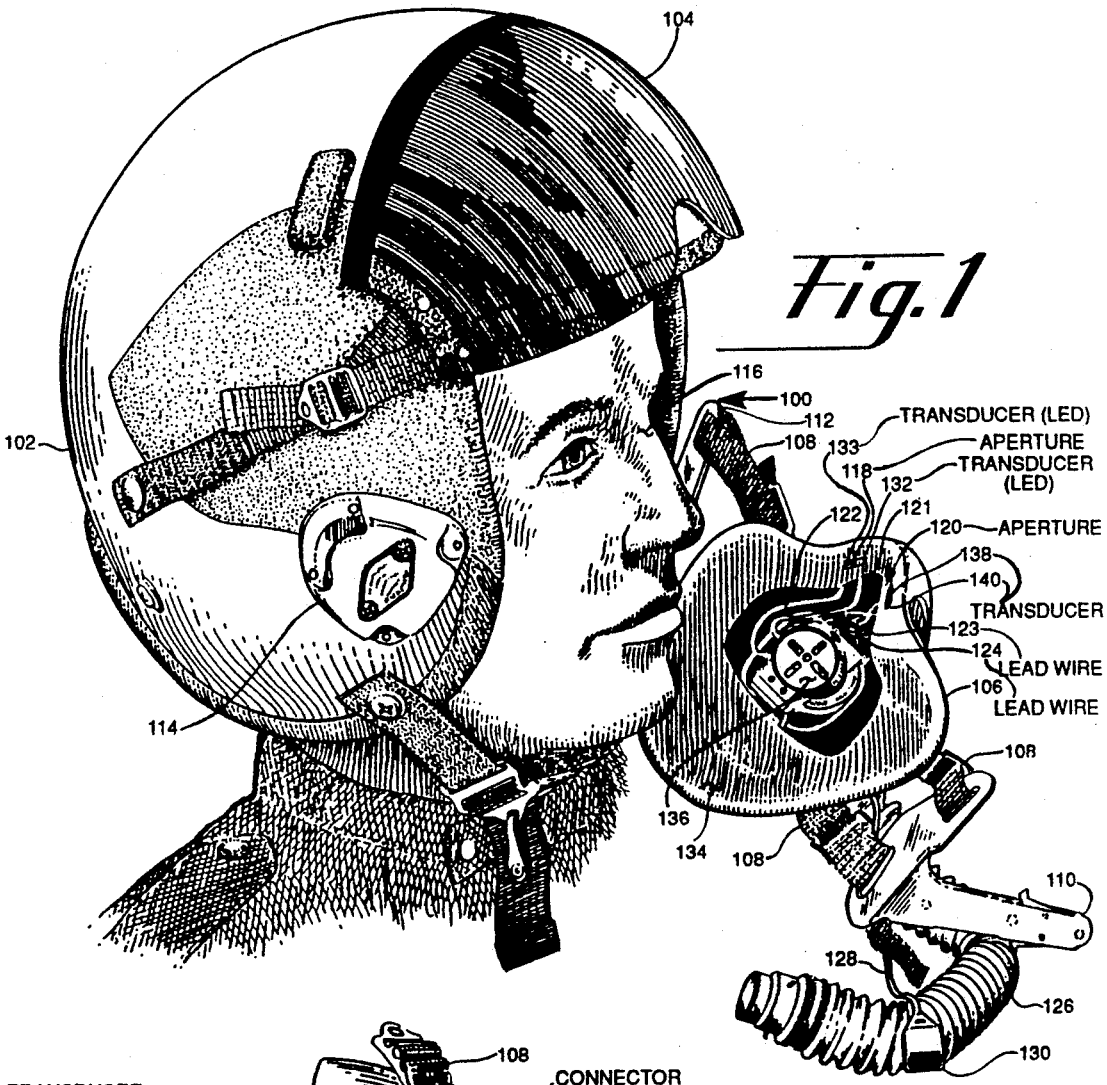
FIG. 1 shows an aircraft pilot and pilot life-support apparatus which includes physiological monitoring in accordance with the invention.

At 100 in FIG. 1 is shown the head portion of an aircraft crew member such as a pilot together with the helmet 102 and oxygen mask 106 portions of the life-support system used by such pilots in tactical and other military aircraft. In the FIG. 1 drawing, the pilot's helmet 102 is shown to include a sun visor 104 and a receptacle 114 by which the oxygen mask 106 is held in place over the nose and mouth portions of the pilot's face. Connecting with the receptacle 114 and a similar not shown receptacle on the opposite side of the helmet 102 are a pair of spring loaded bayonet connectors 110 and 112 to which are attached an array of adjustable webbing members 108 that connect with the mask 106 and provide adjustable tension for holding the mask in position over the pilot's face.

In the U.S. military, it is common practice to mold masks of the type shown at 106 in FIG. 1 to the unique facial features of each user pilot. This custom molding together with the flexible conforming nature of the interior liner 134 portion of the mask 106 enables the array of adjustable webbing members 108 in FIG. 1 to be capable of holding the mask 106 in both a fixed predetermined position and in a relatively immovable position with respect to the pilot's facial features. This property of the mask 106 lends especially well to the present invention additional capabilities or improvements provided for the mask 106.

Additional details of the improved mask 106 which are shown in FIG. 1 include an audio signal to electrical signal transducer or microphone 136 which is disposed in close proximity with the pilot's mouth when the mask 106 is positioned over his face. Also shown in FIG. 1 is the flexible conduit or hose 126 by which oxygen and/or other life-support gases are communicated to the mask 106 and the pilot 100 from sources in the Piloted aircraft. The multiple conductor electrical cable 128 and its attached multiple pin connector serve to connect both the microphone 136 and the physiological state monitoring elements of the invention to electronic circuit apparatus mounted in the aircraft.

The improved mask 106 in FIG. 1 also includes a plurality of elements associated with the physiological monitoring system of the present invention. Among these elements are the apertures 118 and 120 which are disposed in opposed portions of the nose bridge region of the mask interior liner 134. In this arrangement, the apertures 118 and 120 located on opposite sides of the upper nose bridge region or the nasal septal anterior ethmoid artery region 116 of the pilot 100 when the mask 106 is worn. By way of the apertures 118 and 120, the nose bridge region 116 of the pilot 100 is exposed to optical signals originating in one or more electrical to optical transducer devices received in one of the apertures 118 and 120. This nose bridge region is also examined or sensed with an optical to electrical transducer generator of electrical signals that is disposed in the opposite of the apertures 118 and 120.

Figure 2:
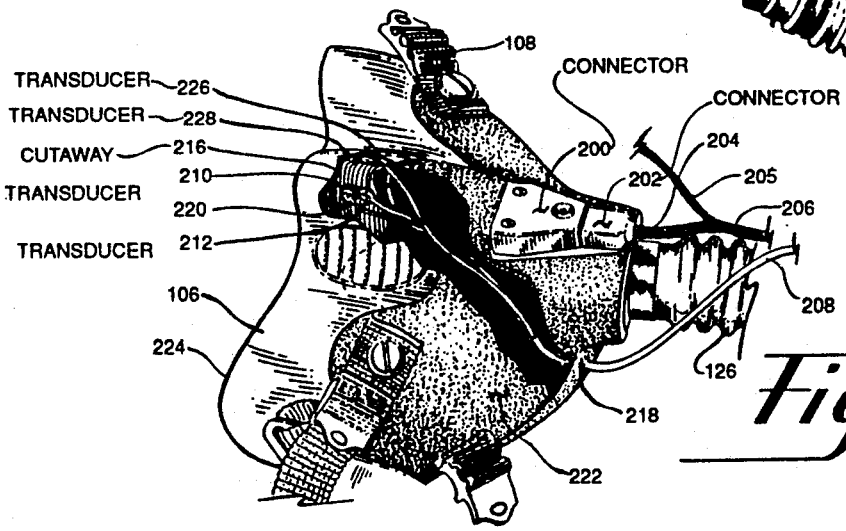
FIG. 2 shows additional details of physiological monitoring sensors from FIG. 1 and adjacent life-support apparatus.

In both FIG. 1 and FIG. 2 of the drawings, a pair of such transducers is shown in both the aperture 118 and the aperture 120 and in the cutaway region 216 of FIG. 2. These transducers are identified with the numbers 132 and 134 for the aperture 118 in FIG. 1 and with the numbers 138 and 140 in the aperture 120. A more comprehensive view of such transducers appears in the cutaway portion 216 of FIG. 2 with the transducers being indicated by the numbers 210, 212, 226 and 228 in the view of FIG. 2.

Electrical lead wires for the transducers 132 and 133 are shown at 121 and 122 in FIG. 1 and the similar lead wires for transducers 138 and 140 are shown at 123 and 124 in FIG. 1. The lead wires 121–124 in FIG. 1 are combined into the multiple conductor electrical cable 128 which also communicates microphone and headphone signals. In FIG. 2, the leads from the transducers 210, 212, 226 and 228 are combined into a multiple conductor cable 208 which is maintained in separation from the microphone transducer and headphone transducer cables 204 and 205. The microphone and headphone leads in FIG. 2 are combined into the separate multiple conductor cable 206 for connection to the aircraft communications system.

According to the present invention, it is contemplated that one pair of the transducers in the apertures 118 and 120 of FIG. 1 function as electrical energy to optical energy converting or transducing devices while the oppositely disposed pair of transducers serve as optical energy to electrical energy converting transducers. By way of this arrangement, density and coloration variations in the optical signal path traversing the pilot's upper nose bridge region are determinative of an electrical signal which is generated by the optical energ to electrical energy group of transducers. This electrical signal, in turn, can be processed into signals which define a number of pilot physiological well-being indicators.

The theoretical aspects of physiological well-being indicators which monitor percentage of hemoglobin molecules saturated with oxygen, pulse rate, pulse waveform, pulse amplitude and pulse absence to gain insight into the physiological state of a human subject are described in the herein incorporated by reference oximeter patents and are additionally described in the list of publications included in the appendix hereof. The U.S. Pat. No. 2,706,927 of Wood et al in the above incorporated by reference group is especially enlightening in this regard. For present purposes, it is sufficient, however, to note that usable physiological signals can be obtained from a pulsating vascular bed located in the nasal septal anterior ethmoid artery region of the pilot 100 through the use of two color responding electrical to optical signal transducers in the apertures of FIG. 1.

For example, the transducers 132 and 133 in the aperture 118 can be made capable of generating two spectrally separated optical signals—signals of, for example, 660 nanometers and 920 nanometers wavelength, (in the red and infrared portion of the electromagnetic spectrum) by employing silicon light emitting diodes as the transducers 132 and 133. Transducers of this type are, for example, found capable of providing electrical output signals from the oppositely disposed optical to electrical transducers, the transducers 138 and 140 in FIG. 1, that distinguish between the presence and absence of bright red oxygenation in the hemoglobin reaching the pilot's nasal region 116. Such signals can also measure the amount of oxygenated hemoglobin reaching the nasal region 116 and can accomplish this measurement during each instant of flight and G-force exposure.

The red and infrared nature of the optical signals generated by light emitting diode embodiments of transducers 132 and 133 can be understood to generate differential amplitude responses in the optical to electrical transducers 138 and 140 in accordance with the amount of red or blue coloration, that is, the amount of oxygenation in the blood of the pilot 100. It is especially desirable that in the FIG. 1 arrangement, this measurement of red or blue coloration and oxygenated blood presence can be accomplished in the cranial adjacent pulsating vascular bed region indicated at 116 in FIG. 1.

In a related manner, optical signals from the region 116 of the pilot 100 are also capable of indicating both the absence of blood flow pulsations in the brain adjacent portions of the pilot and of indicating the quantitative amount or amplitude of these pulsations. The absence of pulsations in the region 116, of course, indicates a blacked-out or GLOC condition in the pilot or the ensuance of a condition in which pulse amplitude degradation and spectral shifts in oxygenated blood predict loss of judgment and other mental functions. The optical to electrical signal transducers 138 and 140 in FIG. 1 may be embodied in the form of silicon solar cells or other preferably solid state optical to electrical transducer devices having spectral responses that are compatible with the selected electrical to optical transducer devices.

The upper nose bridge region of the pilot 100, that is the nasal septal anterior ethmoid artery region 116, is found to be especially desirable for use in monitoring decreased blood flow in an aircraft pilot that is subject to downwardly directed or +Gz acceleration—that is to accelerations which tend to push the pilot more firmly into his seat. Such acceleration forces tend to diminish blood flow to the cerebral or cranial region of the pilot and to include a diminishing of the blood pressure and flow in the carotid artery system which supplies the brain.

The close proximity of the pulsating vascular bed in the nasal septal anterior ethmoid artery region of a human to the carotid artery is found to provide a desirable degree of tight coupling or direct relationship between carotid presence and flow conditions and the conditions sensed in the vascular bed—a relationship that is useful for the present physiological monitoring apparatus. Moreover, the short time delay between carotid artery pressure and flow and pressure and flow in the ethmoid artery region is also desirable for the present invention. Therefore, the pulsations and density and coloration variations sensed in the pulsating vascular bed of the nasal septal anterior ethmoid artery region 116 provide an unusually desirable basis for physiological monitoring.

It is also clear that other regions of a pilot's face or head could be employed for G-force influenced physiological monitoring—especially other regions which may be served by sensors under the oxygen mask 106 or similar pilot life-support apparatus.

Within the oximeter apparatus which receives optical-electrical signals from the region 116 of the pilot 100, a measurement taken in the absence of the pilot's pulse is compared with a measurement taken in the presence of a pulse. This arrangement allows for correction of factors such as the presence of venous blood and tissue in the sensed pulsating vascular bed. Two optical wavelengths are used in the sensing for such instruments in order to calculate the oxygen saturation of arterial blood. The ratio of the absorptions at the two sensing wavelengths is a measure of the percentage of hemoglobin saturation in the illuminated blood. Additional details regarding these measurements are to be found in the above incorporated by reference patents.

Before leaving the FIG. 1 and FIG. 2 drawings, certain of the therein illustrated details are deserving of comment. The oxygen mask shown in FIG. 1 and FIG. 2 is of the P12 type currently used by the U.S. Air Force and other U.S. military. The mask is comprised of a molded hard plastic body member, indicated at 222 in FIG. 2, to which is attached the soft and pliable interior lining portions of the mask—the portions which are resilient and face mating and indicated at 224 in FIG. 2. The mask shown in FIG. 1 and FIG. 2 is fabricated inter alia by Gentec Corporation using the assembly number 60240, and the identification numbers G012-1050-04, however, the invention is not limited to the use of this or any other mask or life-support apparatus.

The apertures 118 and 120 in the mask 106 may, of course, be molded or cut into the nose covering portion of the mask interior liner 134 with the transducers 132, 133, 138 and 140 being received in molded pockets of the interior liner. In small quantity and experimental use these transducers may be attached with materials such as silicon rubber or rubber cement or other attachment arrangements as are known in the resilient material arts. Other arrangements of the apertures 118 and 120 and the transducers, arrangements such as covering the apertures with protective and optical signal transmitting media are, of course, possible and are to be recommended in large quantity fabrications and uses of the invention.

The cutaway portion 216 of the mask in FIG. 2 shows how either the interior surface of the mask liner 134 or a cloth like supplementary element 220 may be used to mount the transducers 210, 212, 226 and 228. A supplementary element of this type is supplied as a portion of the Nellcor D-25 oxisensor array that is preferred for use in embodying the invention.

The elements 200 and 202 which are shown attached to the molded plastic body portion of the FIG. 2 mask are actually portions of the microphone 136 which appears in FIG. 1. The element 202 in FIG. 2 is a removable electrical connector for the microphone signal conductors of the cable 206. The cable 205 connects with the pilot's earphone set. In a more refined version of the FIG. 2 mask, the optical transducer electrical signals of the cable 208 could, of course, be brought out through the elements 200 or 200 and 202 to maximize the degree of pilot convenience in using the FIG. 1 and FIG. 2 apparatus. FIG. 1, in fact, shows the use of a single multiple pin connector for both the audio and optical signal functions of the mask 106. In the FIG. 2 arrangement of the invention, the optical transducer electrical conductors of the cable 208 are shown to be passed through a sealed aperture region 218 of the plastic body member 222. The small recessed area and protruding button indicated at 214 in the element 200 of FIG. 2 serves as a release latch for the element 202.

The mask 106 of FIG. 1 and FIG. 2 is regarded as a relatively short-lived and frequently replaced item of pilot support apparatus in view of its lightweight, resilient and therefore physically vulnerable nature; the disposable nature of the oximeter sensing transducers described in the above recited probe or oximeter sensor patents are conveniently compatible with this disposable nature of the mask 106. In a fully operational arrangement of the FIG. 1 and FIG. 2 mask, the disposable nature of the optical transducer elements therefore adds only a limited degree of cost to the overall mask assembly.

Figure 3:
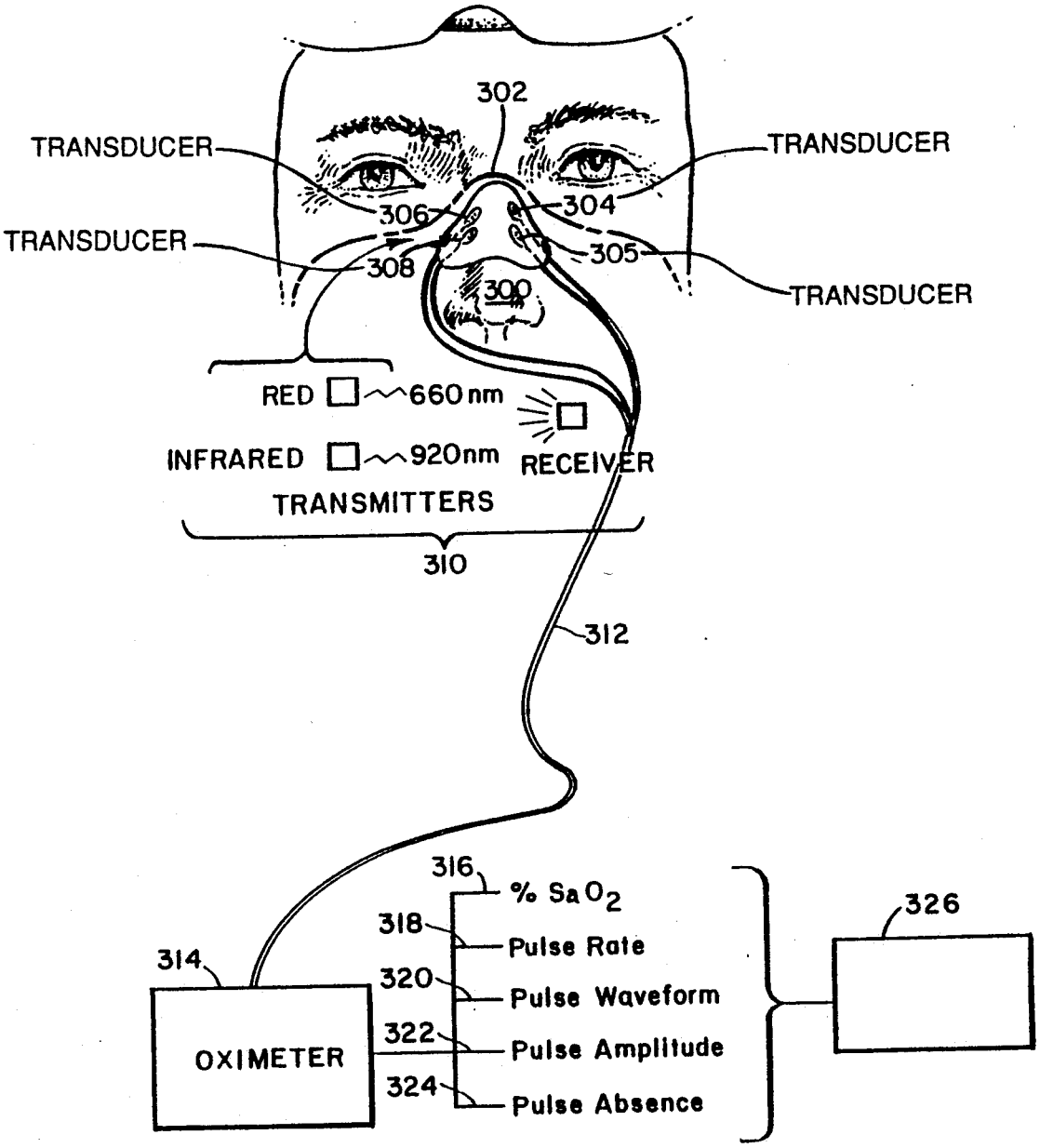
FIG. 3 shows a physiological monitoring system block diagram in accordance with the invention.

FIG. 3 in the drawing shows a block diagram of a system which employs the optical physiological monitoring sensors of FIG. 1 and FIG. 2. In FIG. 3, a group of four transducers 304, 305, 306, and 308 are shown disposed on opposite sides of the upper bridge portion of the pilot's nose 300. The FIG. 3 transducers are held in relative position by a substrate member 302 and the mask of FIGS. 1 and 2 which is not shown in the FIG. 3 view. Alternately, the substrate member 302 can be held in position by an elastic band 328 passing behind the head of the pilot or other monitored subject. Such an elastic band support arrangement is especially desirable for mask-free physiological monitoring uses of the invention outside the aviation art—as a supplement to the previously discussed hospital monitoring sensor arrangements, for example.

The transmitter and receiver nature of the transducers of substrate 302 together with the previously identified optical spectral region preferred for use in the FIG. 3 apparatus are indicated at 310 in FIG. 3 with the indication at 310 suggesting that only one receiver the transducer 304 is used. Signals to and from the transducers in FIG. 3 are conveyed by the multiple conductor cable 312 in communication with the oximeter instrument of block 314. The oximeter 314 may be of the type described in one or more of the above incorporated by reference patents or an instrument manufactured by one of the forty or so instrument suppliers that are currently active in this field. Instruments manufactured by Hewlett Packard Corporation of the San Francisco peninsula region of California or the Nellcor Co. Inc. of Hayward, Calif. are useful at 314 in FIG. 3; the Nellcor N-200 oximeter is preferred. Alternately the oximeter 314 may be of a largely software embodiment as is suggested in the above incorporated by reference patents.

The output signals available from an oximeter of the indicated type are indicated at 316, 318, 320, 322 and 324 in FIG. 3. The nature of these signals is well-known in the medical instrumentation art and is further described in connection with the test subject related data in FIG. 4 and FIG. 5 herein. Use of one or more of the signals 316–324 to actuate a physiological state related apparatus such is an automatic pilot is indicated at 326 in FIG. 3. It is the intent of the present invention that one or more of the signals 216–324 be used as at least a vote in a decision arrangement which ultimately decides that a monitored crewmember such as a pilot is not in a safe physiological condition. An alarm condition or replacement of the pilot's function by an automatic pilot as indicated in FIG. 3 is therefore the ultimate possible use of information generated by the present apparatus. The exact nature of the signals available from an oximeter instrument is also described in the above incorporated by reference patents and in other prior art publications including the references recited in the appendix hereof.

In the FIG. 3 system, a pair of optical energy to electrical energy transducers are shown. This two transducer arrangement is in keeping with the parallel connected receiver transducers in the FIG. 1 and FIG. 2 representations of the invention. In each of the FIGS. 1, 2 and 3 instances, it is intended that the receiver transducer be of the broad optical spectrum type notwithstanding the use of electrical to optical transducer illumination sources that are of the limited spectral output type. The use of electrically parallel connected dual received devices as in FIGS. 1 and 2 and in an arrangement where each receiver is responsive to the optical energy signal originating in both optical energy sources has been found to be desirable when movement or slippage of the transducers on the monitored subject can occur. Two receives also increase the area of reception for the transmitted signals.

The use of a single receiver transducer is found to be acceptable as long as a pilot's mask 106 does not slip excessively in an acceleration environment of the system. Such movement would, of course, move the transmitter/receiver transducers out of a alignment with the upper nose bridge region 116. It is possible that some other number of receiver and transmitter transducers other than the herein described one and two devices may be most practical for a fully optimized embodiment of the invention.

During optical energy transmission through tissue such as the pulsating vascular bed of the upper nose bridge region 116, as indicated in FIG. 1 and FIG. 3 of the drawings, the diffusing effect of the vascular bed tissue precludes the tendency for energy from one optical source to be received principally by one receiver transducer device. Each of the two receiver devices in FIGS. 1, 2, and 3 is therefore responsive to the optical energy output of each of the sources, the sources at 132 and 133, for example. The transducer redundance and the additional active transducing area provided by the two receiver arrangement of FIGS. 1 and 2 are additionally desirable from both the reliability and signal enhancement viewpoints.

The optical spectrum wavelengths indicated at 310 in FIG. 3 are found to be satisfactory from both the oxygenated and deoxygenated hemoglobin spectral absorption viewpoint and additionally for convenience of optical energy generation with low cost and readily available solid state transducers devices. It is, of course, also possible to generate optical energy of the indicated wavelengths using a broad spectrum source such as an incandescent lamp together with appropriate filtering. Optical signals of other spectral frequencies may be desirable in alternate embodiments of the invention and can be achieved with appropriate filters and a broad spectrum source or with solid state electrical to optical transducers having outputs in a selected different portion of the optical spectrum.

Figure 4:
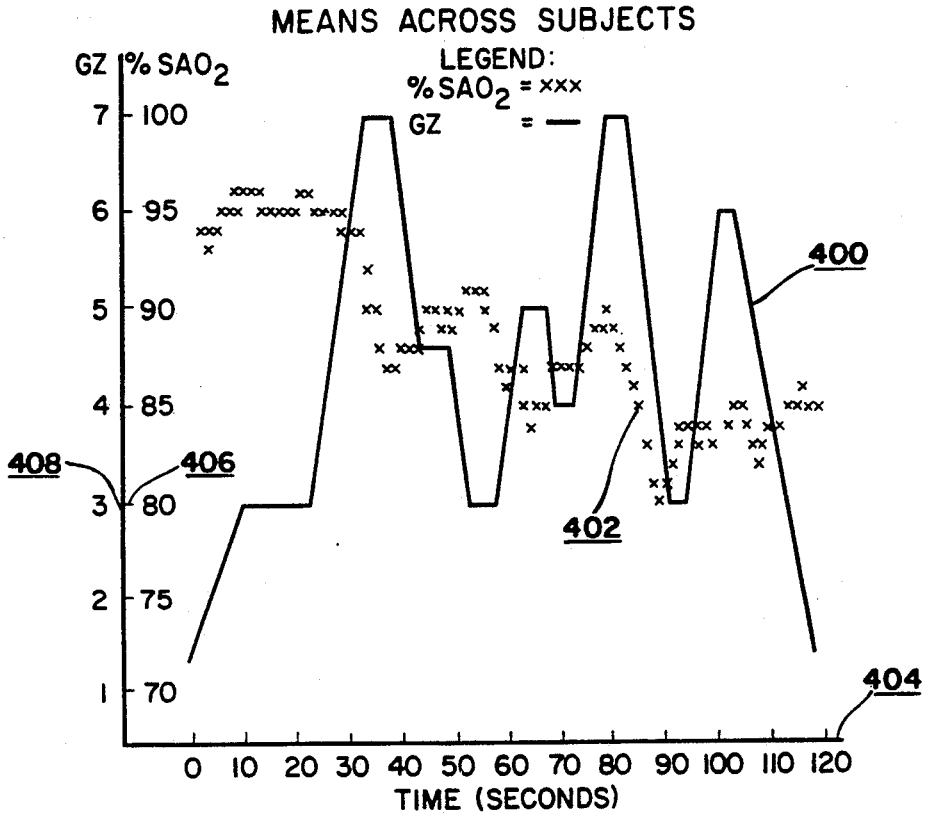
FIG. 4 shows the effect of G-force acceleration on a physiological indicator that is subject to monitoring with the invention.

FIG. 4 in the drawing shows the correlation between G-force environment and one of the principal physiological well-being indicators that is subject to monitoring with the present invention. The FIG. 4 drawing represents a time record of a simulated aerial combat maneuver in which the pilot of an F-16 aircraft, for example, is subjected to 120 seconds of combat maneuvering G-forces including two peaks of seven G amplitude and peaks of five and six G amplitude. The G-force environment in FIG. 4 is indicated by the curve 400 which is used in conjunction with the vertical scale 408. During the interval represented by the curves of FIG. 4, the human test subject is reclined in an F-16 like seat with a 30° seat back angle and is exerting the customary anti-G straining maneuver.

The data of FIG. 4 graphically illustrates the concept proposed by author Barr, in the appendix cited 1962 investigation, that decreases in arterial oxygen saturation, result from increasing G-force. The Barr investigation also focuses on the susceptibility of lung function in a human test subject to changes in G-force environment. Other investigators, including the appendix cited work of Nolan et al in 1963, have found that oximetry measurements taken about the head of a human test subject, do in fact, accurately track cuvette oximetry measurements obtained from blood continuously withdrawn from a radial artery during exposures to accelerations in the 2 to 5 G-range.

One effect of the G-force environment represented by the curve 400 in FIG. 4 is indicated by the curve 402 which is read in conjunction with the vertical scale of percent saturated oxygen at 406. Several aspects of the oxygen saturation curve 402 are notable including the significant fall of percent oxygen saturation from the 95% region to the 86% region following initial onset of a 7 G-force peak. Continued falling of the percent oxygen saturation with intervals of mild recovery during periods of lower G-force and progression to saturation levels in the 80% region are indicated by the latter portions of the curve 402. The delayed direct correlation between G-force magnitude and oxygen saturation is especially notable in the FIG. 4 curve.

The significance of the curve 402 in FIG. 4 can be even better appreciated with the understanding that, generally, saturated oxygen percentages in the 70 to 80% range result in notable losses of cognitive mental ability in a human test subject. Saturation values lower than 82% moreover result in significant mistakes on the part of a test subject and values below 70% are considered an extreme cut off for pilot safety. The operating environment of the present invention is further defined by the generally accepted notion that only three to five seconds of consciousness remain for an aircrew member once a lack of pulse conditions occurs in the carotid artery region.

The notable decrease in hemoglobin oxygen saturation indicated in FIG. 4 has been attributed to a combination of effects including decrease in heart pumping volume, particularly in the end-diastolic volume, stroke volume, and cardiac output. This decrease is also attributed to collapse of the pulmonary alveoli during G-force acceleration; to arterial venous shunting in independent regions of the lungs and to unfavorable effects resulting from G-suit force action on the diaphragm of a human test subject, see the appendix cited work of Vanderberg et al. The data of FIG. 4 represents a composite of the results obtained from eight Air Force volunteers of an average 27 years of age while wearing the U.S. Air Force issued CSU 13/P anti-G suit and breathing atmospheric air by way of an unconnected oxygen mask distal connector.

Figure 5:
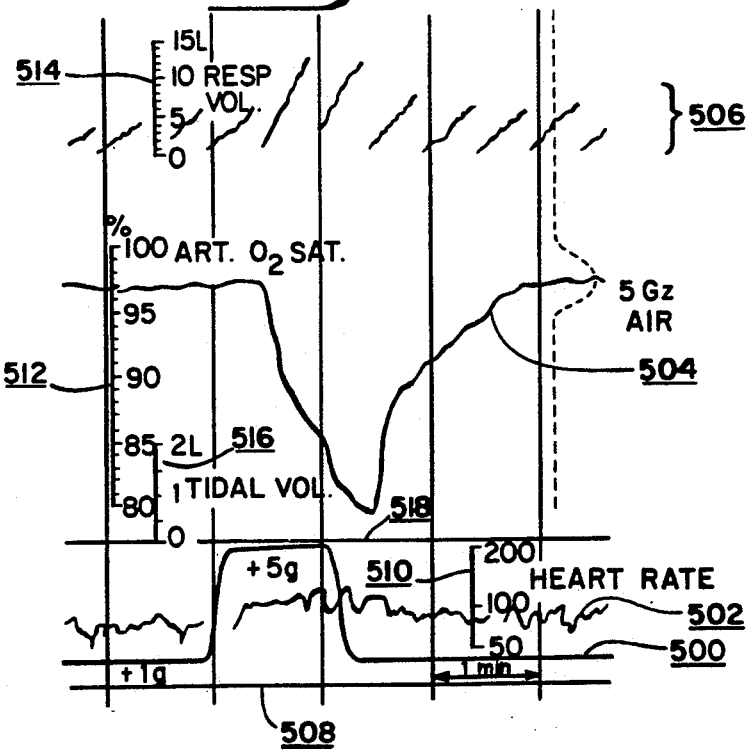
FIG. 5 shows the effect of G-force on a plurality of human physiological indicators.

FIG. 5 in the drawings shows additional response characteristics of a human test subject to the sudden onset of a G-force pulse, the data of FIG. 5 includes respiration volume as indicated at 506 and measured along the scale 514; hemoglobin oxygen saturation as indicated by the curve 504 and measured along the scale 512; heart rate as indicated by the curve 502 and measured along the scale 510 and the G-force pulse as indicated by the curve 500. The lower axis 508 in FIG. 5 indicates time in increments of one minute. Tidal volume, an indication of ventilation efficiency is included at 518 in FIG. 5 with the scale at 516 measuring such tidal volume.

The FIG. 5 drawing confirms the disruptive effect of G-forces on arterial oxygen saturation as well as on respiratory volume and heart rate. Of particular additional significance in the FIG. 5 drawing is the extreme drop in the curve 504 which occurs during and after the +5 g peak shown in curve 500. This interaction between increasing G and decreasing percent arterial oxygen saturation demonstrates the importance of monitoring the physiologic state of the pilot in high performance aircraft.

The data of FIGS. 4 and 5 indicates the influence of G-force incurred in the positive Z direction, that is force tending to urge a pilot more firmly into his seat, on readily measured clinical indications of physiological well being. In a sense therefor, the data of FIGS. 4 and 5 indicate the need for systems of the type herein described and also indicate the range of sensitivities and data variables to be expected as input signals by systems of this type.

The effects and results disclosed in FIGS. 4 and 5 are, however, related to only one of the possible factors making use of non-invasive physiological monitoring of tactical aircrew members desirable. In addition to the G-force incidents represented in FIGS. 4 and 5, a number of other physiological well-being threats frequently are encountered by a tactical aircraft crew member. These other events can include the loss of life-support systems, e.g., the loss of oxygen due to equipment failure or combat damage, and the loss of G-suit operation. Additionally, these threats can include such effects as hyperventilation in which the pilot is subjected to excessive levels of oxygen and becomes involved in a vicious circle sequence of exertion and oxygen saturation that leads to his inability to function.

The monitoring system of the present invention is capable of initiating environmental changes in response to any or a combination of these threatening conditions in a pilot in view of its precise monitoring of the ultimate results of the undesirable condition. The presently described monitoring of the quantitative amount of oxygen present in the circulatory system of a pilot and the accomplishing of this monitoring at a point that is closely connected with the pilot's brain represents a nearly ideal monitoring arrangement. It is also desirable that this monitoring is accomplished in a non-invasive and invisible to the pilot manner. The signals developed by the present optical sensing of a pulsating vascular bed can, of course, be combined with other signals which indicate a deterioration of physiological condition in a pilot—signals such as eye blink sensing, hand grip on control stick measurement, head slump detection, EEG indications and incurred G-force magnitude. Signals of this nature may be combined with the output signals of the present system to provide a correlated or verified physiological condition indicating signal.

The present invention therefore provides an electrode free non-invasive and desirably located sensor arrangement for sensing informative parameters relating to the physiological well-being of a pilot or other persons. The described system has been found capable of functioning even in the extreme conditions of 9 $G_z$ acceleration force and is found to provide results which correlate with invasive arterial sampling of test subjects undergoing G-force or other environmental conditions. The brain proximity of the region sensed by the present monitoring system is especially desirable with respect to time delay considerations and accuracy.

Appendix

The following publications in the field of human test subject physiological monitoring are believed to be of interest with respect to the background of the present invention. Certain of the publications herein listed have been discussed in the preceding text.

Barr, P. Hypoxemia in man induced by prolonged acceleration. Acta Physiol. Scand. 54:128–37, 1962.

Crosbie, R. J. A Servo Controlled Rapid Response Anti G-Valve, NADC, Warminster, PA, 1983 SAFE Meeting, Las Vegas, Nev., 6–8 December 82.

Dhenin, G., Effects of long duration acceleration, *Aviation Medicine*, Trimed Books Limited; London, 1978.

Jennings, T., Seaworth, J., Howell, L., Tripp, L., Ratino, D., and Goodyear, C. The Effect of +Gz Acceleration on Cardiac Volumes Determined by Two-Dimensional Echocardiography. SAFE Journal, Winter Qtr, 1985, Vol 15, No. 4.

Lindberg, E., Sutterer, H., Marshall, R., Headly, R. and Wood, E. 1960. Measurement of Cardiac Output during Headward Acceleration Using the Dye Dilution Technique, *Aerospace Medicine*, 31: 817–834, 1960.

Mackenzie, N. Comparison of pulse oximeter with an ear oximeter and an in-vitro oximeter, *J. of Clin Monitoring*, vol. 1, pp. 156–160, July 85.

New, W. 1985. Pulse Oximetry, *J. of Clin Monitoring*, vol. 1, No. 2, April.

Nolan, A. C., Marshall H. W., Cronin, L., Sutterer, W. F., Wood, E. H. Decreases in arterial oxygen saturation and associated changes in Pressures and Roentgenographic appearance of the Thorax during forward ($G_x$) acceleration. *Aerospace Med.* 1963; 34: 797–813.

Vanderberg, R. A., Nolan, A. C., Reed, J. H., Wood, E. H. Regional pulmonary arterial-venous shunting caused by gravitational and inertial forces. *J. Appl. Physiol.* 1968; 25:516–27.

Yelderman, M., New, W., Evaluation of Pulse Oximetry. *Anesthesiology*, October, 83: Vol 59, No. 4, pp 349–352.

Yoshiva, I., Shimadan, U., Tanoha, K. Spectrophotometric Monitoring of arterial oxygen saturation in the fingertip. *Med Biol Eng Comput* 1980; 18:27–32.

While the apparatus and method herein described constitute a preferred embodiment of the invention, it is to be understood that the invention is not limited to this precise form of apparatus or method, and that changes may be made therein without departing from the scope of the invention, which is defined in the appended claims.

We claim:

1. Aviation life support apparatus comprising the combination of:

a facial communications and oxygen delivery mask member receivable over the nose and lower facial region of an aircrew member;

optical sensing means received in said mask member and in optical communication with a nasal septum region pulsating vascular bed of said aircrew member for sensing G-force loading influenced quantitative blood flow indicators in said vascular bed and adjacent cerebral regions of said aircrew member.

2. The apparatus of claim 1 wherein said pulsating vascular bed includes a nasal septal anterior ethmoid artery region of said aircrew member.

3. The apparatus of claim 1 wherein said optical sensing means includes solid state electrical to optical and optical to electrical signal transducers coupled via optical signal passing through said pulsating vascular bed.

4. The apparatus of claim 3 wherein said electrical to optical signal transducers include a plurality of light emitting diode transducer elements each generating an optical signal of different optical wavelength.

5. The apparatus of claim 4 wherein said different optical wavelengths are selected in response to the optical energy absorption characteristics of hemoglobin.

6. The apparatus of claim 3 wherein said facial mask member includes means closely conformed to facial features of said aircrew member for quickly disposing said mask in the same relative facial position during each use thereof;

whereby consistent and comprehensible electrical signals are generated by said optical sensing means.

7. The apparatus of claim 6 wherein said facial mask member is custom mold fitted to the facial features of each individual aircrew member.

8. The apparatus of claim 3 wherein said mask member includes acoustic communications transducer means and wherein electrical signals attending said electrical to optical and said optical to electrical signal transducers and said acoustic transducer means are communicated from said aircrew member to the surrounding environment via a common tether.

9. The apparatus of claim 5 wherein said electrical to optical signal transducers include separate transducer elements generating optical energy at the wavelengths of six hundred sixty and nine hundred twenty nanometers.

10. Physiological condition monitoring apparatus for a exposed aircrew member comprising the combination of:

a mask member disposed in covering relationship over at least the nosebridge facial region of said aircrew member;

a source of optical energy radiation mounted on said mask member in a first nosebridge facing position thereon;

optical-to-electrical energy transducer means mounted on said member in an opposed second nosebridge facing position thereon, for generating electrical signals representing optical energy signals received from said source of optical energy radiation via blood encolored tissue in the nosebridge region of said G-force exposed aircrew member; and oximeter means for converting said transducer means electrical signals into physiological condition related electrical signals for said G-force exposed aircrew member.

11. The apparatus of claim 10 wherein said source of optical energy radiation and said optical-to-electrical transducer means are received on opposed lateral surfaces of said mask and thereby reside adjacent opposed lateral nose surfaces of said aircrew member while said mask is received in said nosebridge covering relationship.

12. The apparatus of claim 11 wherein said source of optical energy radiation has optical energy output in the red to infrared spectral region.

13. The apparatus of claim 12 wherein said optical-to-electrical energy transducer means includes a plurality of optical-to-electrical transducer elements and said elements are each selectively responsive to energy in a different red to infrared optical spectrum portion.

14. The method of monitoring blood oxygen content in an oxygen mask assisted person comprising the steps of:

illuminating nasal septum facial regions of said person with oxygen mask nose region sourced optical energy of predetermined red to infrared spectral band energy content;

collecting, with oxygen mask nose region located optical-to-electrical signal transducer means, a sample of the optical energy transmitted through blood encolored said nasal septum region tissue of said person; and converting the transducing means electrical signals into physiological condition related electrical signals using a red, and infrared, spectral region dual spectral band oximeter conversion.

15. Oxygen mask apparatus comprising the combination of:

a facial feature conformed enclosure member receivable adjacent nose and mouth structure openings of an oxygen-assisted person, said enclosure member including first and second surface portions extending one along each side of said nose structure of said assisted person;

means for communicating a flow of life-supporting oxygen inclusive gases to and from the space within said enclosure member and thereby to and from said assisted person;

a source of optical illumination mounted on said first surface portion of said enclosure member and directed toward an adjacent lateral nose surface of said assisted person; and optical signals reception means mounted on said enclosure member second surface portion and responsive to the optical illumination signals originating in said source of optical illumination and passed through nose region blood encolored tissue of said person.

* * * * *